United States Patent
Conneway et al.

(10) Patent No.: US 10,471,371 B2
(45) Date of Patent: Nov. 12, 2019

(54) REFLUX CONDENSER METHOD

(71) Applicant: Dow Technology Investments LLC, Midland, MI (US)

(72) Inventors: Fred A. Conneway, Chonburi (TH); Clyde L. Rhodes, II, Scott Depot, WV (US); John F. Szul, Hurricane, WV (US)

(73) Assignee: Dow Technology Investments LLC, Midland, MI (US)

( * ) Notice: Subject to any disclaimer, the term of this patent is extended or adjusted under 35 U.S.C. 154(b) by 70 days.

(21) Appl. No.: 15/590,407

(22) Filed: May 9, 2017

(65) Prior Publication Data

US 2017/0239590 A1 Aug. 24, 2017

Related U.S. Application Data

(62) Division of application No. 12/735,491, filed as application No. PCT/US2009/000121 on Jan. 9, 2009, now abandoned.

(Continued)

(51) Int. Cl.
*B01D 5/00* (2006.01)
*C07C 31/20* (2006.01)
(Continued)

(52) U.S. Cl.
CPC ............. *B01D 5/0063* (2013.01); *B01D 3/04* (2013.01); *B01D 5/0012* (2013.01);
(Continued)

(58) Field of Classification Search
CPC ....... C07D 301/32; C07C 45/78–45/86; C07C 31/18; C07C 31/20; B01D 5/0012;
(Continued)

(56) References Cited

U.S. PATENT DOCUMENTS

| 1,361,910 A | 12/1920 | Schubert |
| 2,771,473 A | 11/1956 | Courter |

(Continued)

FOREIGN PATENT DOCUMENTS

| CA | 978197 | 11/1975 |
| EP | 0181273 | 5/1986 |

(Continued)

OTHER PUBLICATIONS

International Search Report and Written Opinion from related PCT Application PCT/US2009/000121, dated May 6, 2009, (14 pages).

(Continued)

*Primary Examiner* — Jonathan Miller
*Assistant Examiner* — Jonathan Luke Pilcher
(74) *Attorney, Agent, or Firm* — Brooks, Cameron & Huebsch, PLLC

(57) ABSTRACT

Methods, apparatus, and processes are provided for a condenser including flowing a vapor stream including formaldehyde into a tube bundle in a vertical upflow reflux condenser, where a tube in the tube bundle has a length to outside diameter ratio of greater than about 170:1, flowing a cooling fluid on a shell-side of the vertical upflow reflux condenser to condense at least a portion of the vapor stream, where the condensed portion of the vapor stream forms a wetted tube internal surface area on each tube in the generally upright tube bundle; and maintaining the vapor stream velocity at a rate that provides a liquid residence time where formaldehyde condensed on the wetted internal surface area of each tube can react with water to form methylene glycol, removing at least sixty percent (60%) of formaldehyde from the vapor stream fed to the condenser.

9 Claims, 3 Drawing Sheets

Related U.S. Application Data

(60) Provisional application No. 61/062,471, filed on Jan. 25, 2008.

(51) Int. Cl.
  *C07D 301/32* (2006.01)
  *B01D 3/04* (2006.01)

(52) U.S. Cl.
  CPC .......... *C07D 301/32* (2013.01); *B01D 5/0057* (2013.01); *C07C 31/20* (2013.01)

(58) Field of Classification Search
  CPC .... B01D 5/0057; B01D 5/006; B01D 5/0063; B01D 5/009
  See application file for complete search history.

(56) References Cited

U.S. PATENT DOCUMENTS

| | | | |
|---|---|---|---|
| 2,775,600 A | 12/1956 | Maslan | |
| 2,944,966 A | 7/1960 | Eickmeyer | |
| 3,165,539 A | 1/1965 | Lutz | |
| 3,174,262 A | 3/1965 | Lutz | |
| 3,418,338 A | 12/1968 | Gilman et al. | |
| 3,589,689 A * | 6/1971 | English | B01D 3/22 202/158 |
| 3,729,899 A | 5/1973 | Cunningham et al. | |
| 3,745,092 A | 7/1973 | Vanderwater | |
| 3,766,714 A | 10/1973 | Cunningham et al. | |
| 3,904,656 A | 9/1975 | Broz | |
| 3,964,980 A | 6/1976 | Ozero | |
| 4,033,617 A | 7/1977 | Cocuzza et al. | |
| 4,088,699 A * | 5/1978 | Anderson | C07C 45/36 568/560 |
| 4,134,797 A | 1/1979 | Ozero | |
| 4,142,578 A | 3/1979 | Smith | |
| 4,597,833 A | 7/1986 | Néel et al. | |
| 4,726,826 A | 2/1988 | Crawford et al. | |
| 4,848,296 A | 7/1989 | Ahmed et al. | |
| 4,966,657 A | 10/1990 | Delannoy et al. | |
| 4,983,260 A | 1/1991 | Neel et al. | |
| 5,273,572 A * | 12/1993 | Baker | B01D 5/0057 95/254 |
| 5,440,058 A | 8/1995 | Hoffman et al. | |
| 5,529,667 A | 6/1996 | Coffey | |
| 5,840,932 A | 11/1998 | Evans et al. | |
| 6,187,973 B1 | 2/2001 | Husain | |
| 6,209,624 B1 | 4/2001 | Cameron | |
| 6,242,655 B1 | 6/2001 | Husain | |
| 6,437,199 B1 | 8/2002 | Oka et al. | |
| 6,833,057 B1 | 12/2004 | Bessling et al. | |
| 2002/0106316 A1 | 8/2002 | Billig et al. | |
| 2003/0221818 A1 | 12/2003 | Gentry et al. | |
| 2005/0103617 A1 | 5/2005 | Andreis et al. | |

FOREIGN PATENT DOCUMENTS

| | | | |
|---|---|---|---|
| EP | 1208910 | 5/2002 | |
| GB | 174569 | 3/1923 | |
| GB | 174569 A * | 3/1923 | .......... B01D 5/0012 |
| GB | 564646 | 10/1944 | |
| GB | 589547 | 6/1947 | |
| GB | 814119 | 5/1959 | |
| JP | 54016416 | 2/1979 | |
| JP | 52012770 | 3/1987 | |
| WO | 2004056453 | 6/2004 | |
| WO | 2006120207 | 11/2006 | |

OTHER PUBLICATIONS

Tom Cleveland, Hwaili Soo, "Meteor Revolution", Hydrocarbon Engineering, Oct. 2001, (3 pages).
Zhang Xiangyu, "A Comparison of EO/EG Process Technologies", Sinopec Shanghai Engineering Co., 2006, (10 pages).
International Preliminary Report on Patentability from related PCT Application PCT/US2009/000121, dated May 17, 2010 (11 pgs).

\* cited by examiner

REFLUX CONDENSER METHOD

This application is a Divisional Application of U.S. National Stage application Ser. No. 12/735,491, filed Nov. 21, 2011 and published as U.S. Publication No. 2012/0088910 A1 on Apr. 12, 2012, which claims the benefit of International Application Number PCT/US2009/000121, filed Jan. 9, 2009 and published as WO 2009/094103 on Jul. 30, 2009, which claims the benefit to U.S. Provisional Application 61/062,471, filed Jan. 25, 2008, the entire contents of which are incorporated herein by reference in its entirety.

FIELD OF THE DISCLOSURE

This disclosure relates to a process and system for removing formaldehyde from a vapor stream containing the same. More particularly, this disclosure relates to an improved process for condensing a vapor feed stream containing formaldehyde to remove formaldehyde from the vapor feed stream and recover a desired product.

BACKGROUND

When ethylene oxide is prepared by a silver catalyzed, vapor phase, partial oxidation of ethylene with molecular oxygen, a gaseous reaction effluent is obtained. This effluent can be extremely dilute with respect to the desired ethylene oxide product, containing, for example, from about 0.3 mole percent to about 5 mole percent of the desired material.

Since the ethylene oxide effluent is very dilute in the gaseous mixture produced from the oxidation reaction, this mixture is subsequently subjected to various treatments (absorptions, distillations, flash, and the like) in order to obtain pure ethylene oxide. However, these treatments do not sufficiently deal with low concentrations (e.g., concentrations measured in mole parts per million (ppm)) of formaldehyde impurities which can be present in the ethylene oxide sought to be purified.

For example, in some processes, formaldehyde can be removed as an overhead stream following condensation of the ethylene oxide from a stripping column, however, this has several disadvantages. If the formaldehyde concentration in the overhead stream is high, a solid paraformaldehyde phase can form in the overhead system of the column which can result in blockage and erratic operation and can possibly require shutdown and cleanout. See, e.g., J. Frederic Walker, Formaldehyde, pgs. 140-163 (3d Ed. Reinhold Publishing Corp.). On the other hand, in this process, if the overhead stream contains a low formaldehyde concentration, the relative amount of ethylene oxide therein could be excessive, resulting in yield loss of desired purified material.

SUMMARY

Embodiments of the present disclosure provide processes and apparatuses for removing formaldehyde from a vapor feed stream. Embodiments are adaptable to commercial scale ethylene oxide production.

As used herein, an "ethylene oxide recovery column," or "column," refers to, for example, a generally upright, cylindrical column or tower containing plates and/or packing elements, where the plates and packing elements provide a surface area for a liquid and a gas to come into contact, facilitating mass transfer between the liquid and the gas. As will be appreciated, the column can also have other shapes and general orientations, including a polygonal shaped column that is positioned in a horizontal orientation. The ethylene oxide recovery column includes a stripping portion and a reabsorption portion.

As used herein, the "stripping portion" is the section of the column where one or more components of an aqueous solution are removed by being placed in contact with a gas stream that is largely insoluble in the aqueous solution or by heating the aqueous solution to cause a phase change in the one or more components to be removed. In embodiments discussed herein, stripping can be performed on the aqueous solution to purify, recover, and/or separate ethylene oxide, where the "aqueous solution" can be defined as a mixture of ethylene oxide, water, and other compounds, in liquid form.

As used herein, the "reabsorbing portion" is the section of the column where components of a gas are removed by contacting the gas with a relatively nonvolatile liquid solvent that absorbs some components of the gas while not absorbing others. Reabsorbing can be employed to remove trace components from gas streams.

As used herein, a "condenser" is a device that converts vapor into liquid. In embodiments discussed herein, a vapor feed can enter the condenser, where some compounds in the gas phase portion of the first aqueous solution condense while other compounds pass through the condenser and remain in the gas phase. Also, as used herein, a "reflux condenser" is a condenser where vapor condenses and can flow back into the vessel as a reflux stream.

As used herein, "exit entrainment velocity" is the velocity of the gas exiting the tube bundle at or above which some of the liquid becomes entrained in the vapor exiting the tube bundle.

As used herein, a "tube sheet" refers to an apparatus that is connected to the tubes in the tube bundle at each end. The tube sheet can serve to hold the tubes in place and physically contain the shell side fluid.

DETAILED DESCRIPTION

Figure 1A:
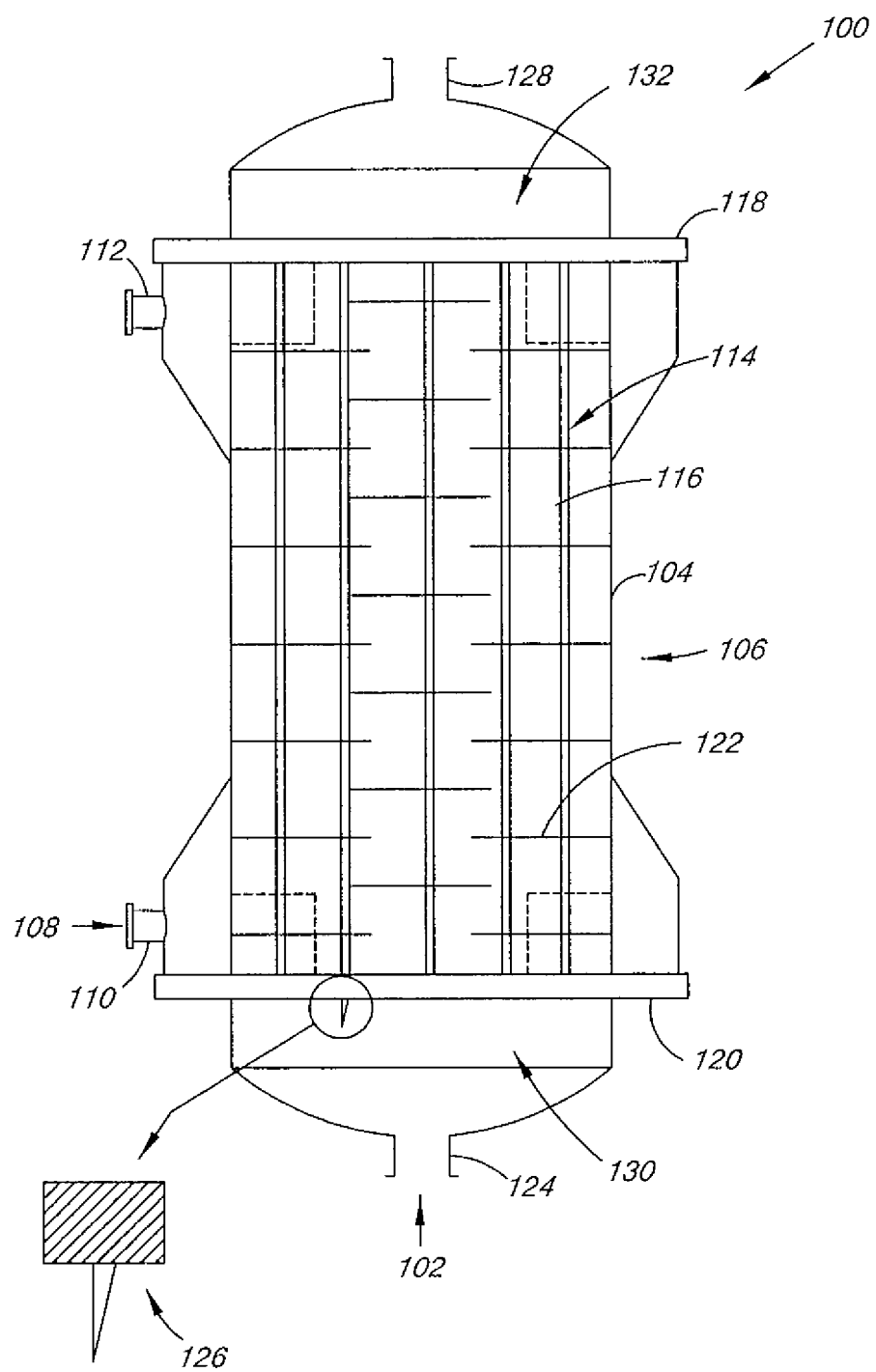
FIGS. 1A and 1B provide an illustration of an embodiment of a condenser of the present disclosure.

Embodiments of the present disclosure include methods and apparatuses for removing formaldehyde from a vapor stream introduced into a condenser. The apparatus embodiments include a condenser including elements arranged, sized, and dimensioned to remove at least sixty percent (60%) formaldehyde from a vapor stream to the condenser.

Embodiments of the present disclosure remove formaldehyde from a vapor stream entering a condenser. The condenser includes a main body defining a cooling zone, where the main body includes a cooling fluid inlet and a cooling fluid outlet to pass a cooling fluid on a shell side of the condenser, and a generally upright tube bundle disposed in the cooling zone to receive the vapor feed. The tube bundle provides an internal surface area for condensing at least some of the vapor feed as heat is removed by the cooling fluid. The condenser also includes a top tubesheet positioned at a top of the tube bundle, where entrained fluid exiting the tube bundle disengages from the vapor stream, falls on the top tubesheet, and flows down the internal surface area of each tube in the tube bundle to provide a wetted internal surface area. Thus, formaldehyde in the vapor feed reacts with water on the wetted internal surface area to form methylene glycol, removing at least sixty percent (60%) of formaldehyde in the vapor stream fed to the condenser.

Some embodiments of the present disclosure remove formaldehyde from an aqueous solution containing ethylene oxide, for example, in an ethylene oxide process where ethylene oxide is the desired product. Embodiments of the present disclosure, however, are not limited to ethylene oxide processes, but rather can be used in other processes where the removal of formaldehyde is beneficial.

The removal of formaldehyde can be beneficial to reduce formaldehyde reactions in refining equipment that can lead to quality problems in a desired product. As an example, in an ethylene oxide process, formaldehyde can react in refining equipment to form byproducts (e.g., condensation products) which can lead to failure to meet ultra violet (UV) specifications in refined monoethylene glycol (MEG), an end-use product of ethylene oxide.

Embodiments of the present disclosure include a shell and tube heat exchanger that condenses a portion of the vapor stream containing formaldehyde entering the heat exchanger, thus, the heat exchanger is termed a condenser. The condenser can consist of a shell with a bundle of tubes inside it. One fluid runs through the tubes, and another fluid flows over the tubes (through the shell) to transfer heat between the two fluids. The set of tubes is called a tube bundle, and may be composed of several types of tubes: plain, longitudinally finned, etc.

The two fluids, of different starting temperatures, flow through the condenser. One flows through the tubes (the tube side) and the other flows outside the tubes but inside the shell (the shell side). Heat is transferred from one fluid to the other through the tube walls, either from tube side to shell side, or vice versa. In order to transfer heat efficiently, a large heat transfer area should be used, therefore the condenser can include many tubes, as discussed herein.

In embodiments of the present disclosure, heat is transferred from the vapor stream entering the condenser to the cooling fluid flowing through the condenser shell side. As heat is transferred, the temperature of the vapor stream decreases, causing components in the vapor stream to condense into a liquid. By controlling, for example, the flow rate of the vapor stream, the cooling fluid flow rate, and the length of the tube bundle, among other operating conditions, the condenser can be designed to maximize the removal of certain components, for example, formaldehyde.

Besides monitoring flow rates and heat transfer surface areas, however, one skilled in the art will appreciate that reactions involving formaldehyde can also affect the removal and the rate of removal of formaldehyde. As shown in Formula (I), formaldehyde can react with water in a reversible reaction to form methylene glycol.

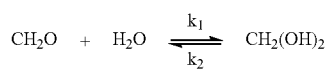

Formula (I)

where $k_1 \ll k_2$. (*Zietschrift fur Physikalische Chemie Neue*, Bd 65, S. 221-224 (1969)). Also, formaldehyde can polymerize to produce, for example, polyoxymethylene, among other polymers.

In embodiments of the present disclosure, the conversion of formaldehyde to methylene glycol is a desired reaction since methylene glycol has a higher boiling point (approximately ninety (90) degrees Celsius (° C.)) as compared to formaldehyde (approximately negative nineteen (−19)° C.). David R. Lide, *Handbook of Chemistry and Physics*, Pub. 2005, Pages 3-262, 6-41. Thus, methylene glycol will condense into a liquid more readily than formaldehyde, enhancing the removal of formaldehyde from the vapor stream entering the condenser.

On the other hand, the conversion of formaldehyde to various polymers is not a desired reaction. In some embodiments, polymers that form on the internal surface of the tubes in the tube bundle can build up on the internal surface, clogging the tubes. To prevent the formation of polymers, thus, embodiments of the present disclosure provide methods and apparatuses for maintaining a wetted internal surface area to promote the methylene glycol reaction and to prevent the polymerization reaction.

FIG. 1A is an illustration of a condenser 100 according to embodiments of the present disclosure. As discussed herein, the condenser 100 can include elements arranged, sized, and dimensioned to remove at least sixty percent (60%) formaldehyde from a vapor stream 102 fed to the condenser 100. In some embodiments, the condenser 100 can remove at least eighty percent (80%) formaldehyde from the vapor stream 102 feed. In various embodiments, the condenser 100 can remove at least eighty-five percent (85%) formaldehyde from the vapor stream 102 feed. The condenser 100 includes a main body 104, or exterior shell, defining a cooling zone 106. The cooling zone 106 is where heat is transferred from the vapor stream 102 to a cooling fluid 108.

In some embodiments, the main body 104 can have a generally circular cross sectional shape. Other shapes are also possible, including ovular, or polygonal. The internal diameter of the main body 104, in embodiments including a circular main body 104, can range from about one hundred (100) inches (2.54 meters) to about two hundred fifty (250) inches (6.35 meters).

In embodiments of the present disclosure, the main body 104 includes a cooling fluid inlet 110 and a cooling fluid outlet 112, where cooling fluid 108 is passed into the cooling fluid inlet 110 to circulate through the main body 104 on a shell side of the condenser 100. In some embodiments, the cooling fluid 108 can be water, however, embodiments are not so limited.

As shown in FIG. 1, the condenser 100 includes a generally upright tube bundle 114 comprised of a number of vertically oriented tubes 116. The tube bundle 114 is disposed in the cooling zone 106 of the main body 104. In some embodiments, the tube bundle 114 can be affixed in position within the main body 104 using a top tubesheet 118, a bottom tubesheet 120, and, in some embodiments, a number of baffles 122. Other means for supporting the tube bundle 114 are also possible.

Figure 1B:
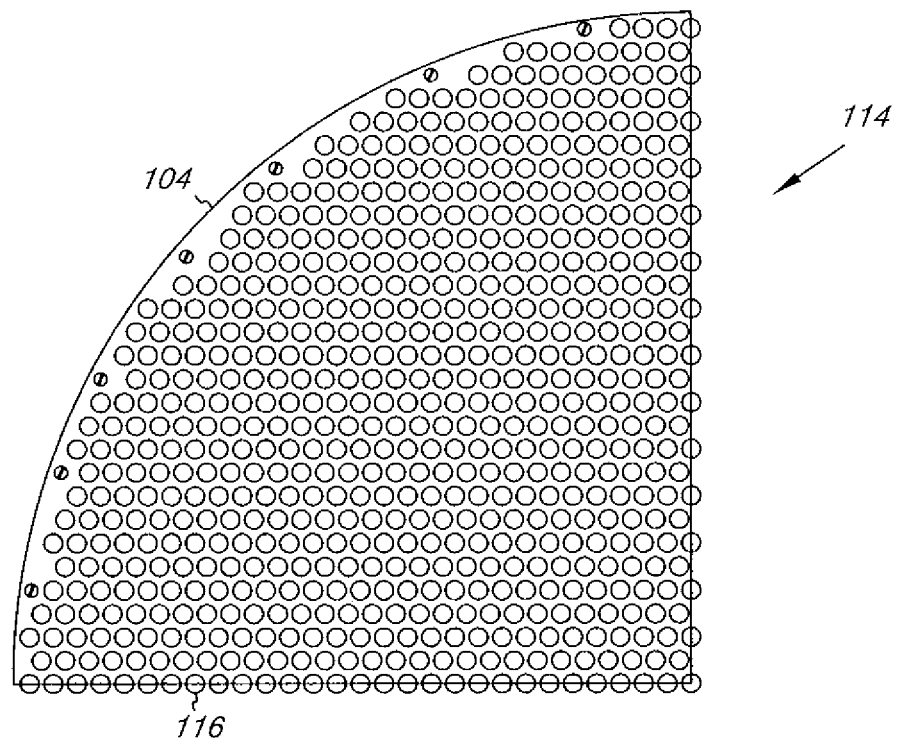

The tubes 116 in the tube bundle 114 can be spaced apart to permit cooling fluid 108 to circulate between adjacent tubes 116 and remove heat from the tubes 116. For purposes of illustration, only a small number of tubes 116 are shown in FIG. 1, also the spacing between the tubes 116 is exaggerated, again for purposes of illustration. FIG. 1B illustrates an embodiment of a cross-section of the tubes 116 as they can be arranged in the tube bundle 114 inside the main body 104. Other configurations are also possible.

In some embodiments, the tube bundle 114 has a ratio of total tube internal surface area to tube internal volume of at least approximately 20:1. In addition, in some embodiments, each tube 116 in the tube bundle 114 can have a length to diameter ratio of at least approximately 150:1. For example, embodiments of the present disclosure include condensers 100 having tubes 116 with an outside diameter in a range of about 0.50 inches (1.27 centimeters (cm)) to about 2.5 inches (6.35 cm) and an internal diameter in a range of about 0.37 inches (0.94 cm) to about 2.37 inches (6.02 cm). In such embodiments, the number of tubes 116 in the tube bundle can range from 1,000 to 115,000 depending on the size of the condenser 100. In addition, the length of the tubes 116 can range from, for example, about 21 feet (6.40 meters) to about 40 feet (12.19 meters). Thus, the tube length to outside diameter ratio can range from, for example, about 170:1 to about 960:1 and the ratio of total tube internal surface area to tube internal volume can range from about 20:1 to about 130:1. Embodiments of the present disclosure, however, are not limited to these dimensions.

The tubes 116 can be formed of a material that can conduct heat through the width of the tubes 116. In addition, the tube material can be chosen to withstand thermal stresses that may occur during operation, for example, due to thermal expansion that can occur at various temperatures and/or stress from high pressures from the fluids themselves. The tubes 116 can also be formed of a material compatible with both the shell side and tube side fluids for long periods under the operating conditions (temperatures, pressures, pH, etc.) to minimize deterioration such as corrosion.

As discussed herein, the tubes 116 can be held in place within the exterior shell 104 via the top tube sheet 118 and the bottom tubesheet 120. Various types of additional supports can be provided between the top 118 and bottom tubesheets 120 to further stabilize the tube bundle 114. These supports can include additional tubesheets, various types of brackets, and/or a number of baffles 122. In some embodiments, the baffles 122 can direct the flow of the cooling fluid 108 through the main body 104 cooling zone 106. In some embodiments, the baffles 120 can range from approximately ten (10) to twenty (20).

The bottom tubesheet 120 can have openings which allow the vapor stream 102 to enter the tubes 116 from a condenser inlet 124. In some embodiments, the tubes 116 may extend through the bottom tubesheet 120. In such embodiments, the tubes 116 can have a tapered bottom 126, as shown in FIG. 1, discussed further herein. The tubes 116 are connected to the top tubesheet 118, which permits a portion of the vapor stream, or in some embodiments, an ethylene oxide rich vapor stream, to exit the condenser 100 through a condenser outlet 128 while liquid exiting the tubes 116 can fall onto the top tubesheet 118 and flow back down the interior surface of the tubes 116.

As discussed herein, the condenser 100 also includes a condenser inlet 124 and a condenser outlet 128. In embodiments of the present disclosure, a vapor stream 102 including formaldehyde can be introduced into the condenser 100 through the condenser inlet 124. From the condenser inlet 124, the vapor stream can enter the tubes 116. To condense a portion of the vapor stream entering the condenser 100, the cooling fluid 108 is introduced to the condenser 100 via cooling fluid inlet 110, where the cooling fluid flows through the condenser 100 on the shell-side, and exits the condenser 100 via the cooling fluid outlet 112.

As discussed herein, as the vapor stream 102 flows from the inlet 130 of the tube bundle 114 to the outlet 132 of the tube bundle 114, a portion of the vapor stream 102 condenses into a liquid. The liquid condensate, or "reflux" flows down the internal surface of the tubes 116, providing a wetted tube surface. The vapor stream 102 and liquid condensate, thus, flow in a countercurrent direction relative each other inside the tubes 116. The cooling fluid 108, therefore, flows in a countercurrent direction relative to the liquid condensate.

As one skilled in the art will appreciate, in the operation of most liquid reflux condensers, a limiting factor in the design and operation of the condenser 100 can occur when vapor velocity at the tube inlet 130 inhibits condensate downflow from the condenser 100, a concept known as "flooding." In other words, flooding occurs when the liquid is carried upwards by vapor instead of draining out by gravity. In the present disclosure, a calculated critical flooding velocity, as used herein, refers to the vapor stream velocity at which the vapor stream velocity at the tube inlet 130 inhibits condensate downflow through the tubes 116 in the tube bundle 114. In embodiments of the present disclosure, the inlet and outlet flooding calculations are taken from the computer program Heat Transfer Research, Inc. (HTRI) Xchanger Suite® 5.0.

In some embodiments, the vapor stream velocity is approximately ninety percent (90%) or less of the calculated critical flooding velocity at the inlet 130 of the tube bundle 114. Additionally, in various embodiments, the vapor stream velocity can be approximately 8.5 feet per second (2.59 meters per second) or less.

Although flooding can occur when the vapor stream velocity is greater than the calculated critical flooding velocity, flooding is also impacted by the geometry of the tubes 116. As such, in some embodiments, each tube 114 in the tube bundle 116 can include a tapered bottom portion 126. In such embodiments, the bottom portion 126 of the tube 116 can extend past the bottom tube sheet 120. The tapered bottom portions 126 increase the effective cross sectional area of the inlet of the tubes 116. By increasing the cross-sectional area of the inlet of the tubes 116, the calculated critical flooding velocity is higher as compared to when the tubes 116 do not include a tapered bottom portion 126 extending past the bottom tube sheet 120.

Flooding can also occur at different places within a tube 116, depending on the vapor stream and liquid condensate flow rates. For example, flooding at the outlet 132 of the tube 116 can also occur, a phenomenon known as droplet entrainment, where vapor leaving the tubes 116 entrains liquid droplets out of the condenser 100. Embodiments of the present disclosure use a vapor stream flow rate into the tube bundle 114 that provides a vapor stream exit velocity in excess of a critical exit entrainment velocity. As used herein, the "critical exit entrainment velocity" refers to the velocity of the gas exiting the tube bundle 114 at or above which some of the liquid becomes entrained in the vapor exiting the tube bundle 114. In some embodiments, the vapor stream exit velocity is greater than approximately two hundred percent (200%) of the critical exit entrainment velocity. In various embodiments, the vapor stream exit velocity can be at least one hundred fifty percent (150%) of the critical exit entrainment velocity.

In various embodiments, the vapor stream exit velocity can be operated at a minimum of one hundred percent (100%) of the critical exit entrainment velocity. As the vapor stream exit velocity is decreased below 100% of the critical exit entrainment velocity, it is possible that the entire length of the internal surface area of the tubes 116 would not remain wetted. In such instances, it is possible that formaldehyde can react to form polymers on the internal surface area of the tubes 116, as discussed herein. Such reactions can cause clogging, or fouling, inside the tubes 116.

When the liquid droplets get carried out of the tube outlets 132, the liquid droplets are sprayed out of the top of the tubes 116, where the liquid droplets can disengage from the vapor and fall onto the top tubesheet 118. The liquid droplets collect and flow back down the tubes 116 in the tube bundle 114. By flowing the vapor stream 102 at a velocity in excess of the critical exit entrainment velocity, the likelihood of having tube wetting along the entire internal surface of the tubes 116 can be improved.

In addition, in some embodiments, the vapor stream velocity can be monitored to provide adequate liquid residence time for the formaldehyde to react with the water. In some embodiments, vapor stream velocity allows for a liquid residence time of at least approximately 0.5 seconds.

As discussed herein, the removal of formaldehyde can be increased by encouraging the reaction between formaldehyde and water to form methylene glycol. By providing a wetted surface, formaldehyde in the vapor stream can react readily with water on the wetted surface to form methylene glycol. Since methylene glycol has a higher boiling point than formaldehyde, as discussed herein, the methylene glycol produced from the reaction can readily condense into a liquid and drain down the internal surface area of the tubes. As such, the removal of formaldehyde is dependent on the amount of surface area available for reaction and heat transfer. By providing a tube bundle 114 with a total tube internal surface area to tube internal volume of at least approximately 20:1 and tubes having a length to diameter ratio of at least approximately 150:1, as discussed herein, the condenser 100 of the present disclosure can remove at least sixty percent (60%) formaldehyde from the vapor stream.

As discussed herein, the condenser of the present disclosure can be used in an ethylene oxide process, where formaldehyde is removed from a vapor stream containing ethylene oxide. In such embodiments, the condenser can be located inside an ethylene oxide recovery column between a stripping portion and a reabsorbing portion of the column, where the vapor stream is produced in the stripping portion of the column.

Before ethylene oxide can be recovered from the ethylene oxide recovery column, however, several steps can be performed. As described herein, the steps to produce ethylene oxide and to use ethylene oxide in further reactions can occur in one place, for example, in an ethylene oxide processing plant. The various steps, however, can also occur in separate facilities.

Alkylenes (olefins) employed in the process of this disclosure can be characterized by the following structural formula (I):

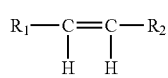

(I)

wherein $R_1$ and $R_2$ are each individually selected from hydrogen and lower monovalent radicals, preferably $C_1$-$C_6$ alkyl radicals including methyl, ethyl, propyl, butyl, and higher homologues having up to six carbon atoms. Preferably, $R_1$ and $R_2$ are each individually selected from hydrogen, methyl, and ethyl. More preferably, each $R_1$ and $R_2$ is hydrogen, and the preferred olefin is ethylene. The corresponding alkylene oxides produced in the process of this disclosure are preferably characterized by the following structural formula (II):

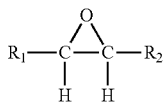

(II)

wherein $R_1$ and $R_2$ are identified herein in connection with the reactant olefin. Most preferably, the alkylene oxide is ethylene oxide (i.e., $R_1$ and $R_2$ are both hydrogen).

Oxygen may be provided to the process as pure molecular oxygen. Alternatively, oxygen may be provided as an oxygen-containing gas, where the gas further contains one or more gaseous components, for example, gaseous diluents such as nitrogen, helium, methane, and argon, which are essentially inert with respect to the oxidation process. In some embodiments, a suitable oxygen-containing gas is air. Additionally, the oxygen-containing gas may contain one or more of the following gaseous components: water, carbon dioxide, and various gaseous promoters and/or gaseous by-product inhibitors, as discussed herein.

The relative volumetric ratio of alkylene to oxygen in the feed gas may range in accordance with any of such known conventional values. Typically, the volumetric ratio of alkylene to oxygen in the feed may vary from about 2:1 to about 6:1. Likewise, the quantity of inert gases, diluents, or other gaseous components such as water, carbon dioxide, and gaseous promoters and gaseous by-product inhibitors, may vary in accordance with known conventional ranges as found in the art.

The present disclosure is applicable to epoxidation reactions in any suitable reactor, for example, fixed bed reactors, fixed bed tubular reactors, continuous stirred tank reactors (CSTRs), and fluid bed reactors, a wide variety of which are well known in the art. The desirability of recycling unreacted feed, employing a single-pass system, or using successive reactions to increase ethylene conversion by employing reactors in a series arrangement can also be readily determined by those skilled in the art.

The particular mode of operations selected can be dictated by process economics. Conversion of alkylene (olefin), preferably ethylene, to alkylene oxide, preferably ethylene oxide, can be carried out, for example, by continuously introducing a feed stream containing alkylene (e.g., ethylene) and oxygen, or an oxygen-containing gas, to a catalyst-containing reactor at a temperature of from about two hundred (200) degrees Celsius (° C.) to about three hundred (300)° C., and a pressure which may be in a range of from approximately five (5) atmospheres (five hundred six (506) kilopascals (kPa)) to approximately thirty atmospheres (3040 kPa) depending on the mass velocity and productivity desired. Residence times in large scale reactors can be on the order of about 0.1 to about five (5) seconds. The resulting alkylene oxide, preferably ethylene oxide, can then be separated and recovered from the reaction products using further processes.

The alkylene oxide produced according to the present disclosure may be converted into alkylene glycols, alkanolamines, and glycol ethers. Ethylene glycol can be used in two applications: as a raw material for poly(ethylene terephthalate) for use in polyester fiber, film, and containers, and as automotive antifreeze. Also, di-, tri-, and tetraethylene glycols are coproducts of ethylene glycol.

Ethylene glycol can be produced by the (catalyzed or uncatalyzed) hydrolysis of ethylene oxide. Ethylene oxide hydrolysis can proceed with either acid or base catalysis or uncatalyzed in neutral medium. Acid catalyzed hydrolysis activates the ethylene oxide by protonation for the reaction with water. Base catalyzed hydrolysis, however, results in considerably lower selectivity to ethylene glycol, producing diethylene glycol and higher glycols (e.g., triethylene and tetraethylene glycols) in addition to the ethylene glycol. Ethylene glycol monoethers can be manufactured by the reaction of an alcohol with ethylene oxide. Also, ethanolamine can be manufactured by the reaction of ethylene oxide with ammonia. See, for example, U.S. Pat. No. 4,845,296.

In some embodiments, the per-pass conversion of ethylene to ethylene oxide can be low (i.e., on the order of one (1) percent or less), producing a mixture containing dilute concentrations of ethylene oxide along with unreacted ethylene and oxygen, aldehydes, acidic impurities, nitrogen, and argon, among others. In some embodiments, the aldehydes can include formaldehyde and acetaldehyde. In some embodiments, the per-pass conversion of ethylene to ethylene oxide can range from five (5) percent to twenty-five (25) percent.

The dilute ethylene oxide mixture obtained can be scrubbed in an absorber with water to form an aqueous solution including ethylene oxide and to thereby separate the ethylene oxide from the unreacted ethylene and oxygen and other gaseous components of the reaction mixture (e.g., carbon dioxide, nitrogen, argon). The remaining separated gaseous materials can be recycled as cycle gas to be mixed with the feedstock of ethylene and pure oxygen.

The aqueous solution is then passed to the ethylene oxide recovery column including the condenser of the present disclosure, where the aqueous solution is used to produce an ethylene oxide stream with a higher ethylene oxide weight percent. The ethylene oxide stream can be removed from the column and passed to other equipment in the ethylene oxide processing plant for further purification or for use in other reactions. For example, in some embodiments, the ethylene oxide stream can be routed to a glycol unit reactor, where ethylene oxide is converted to ethylene glycol by reaction with water. The ethylene glycol produced can be monoethylene glycol, diethylene glycol, and/or triethylene glycol.

Figure 2:
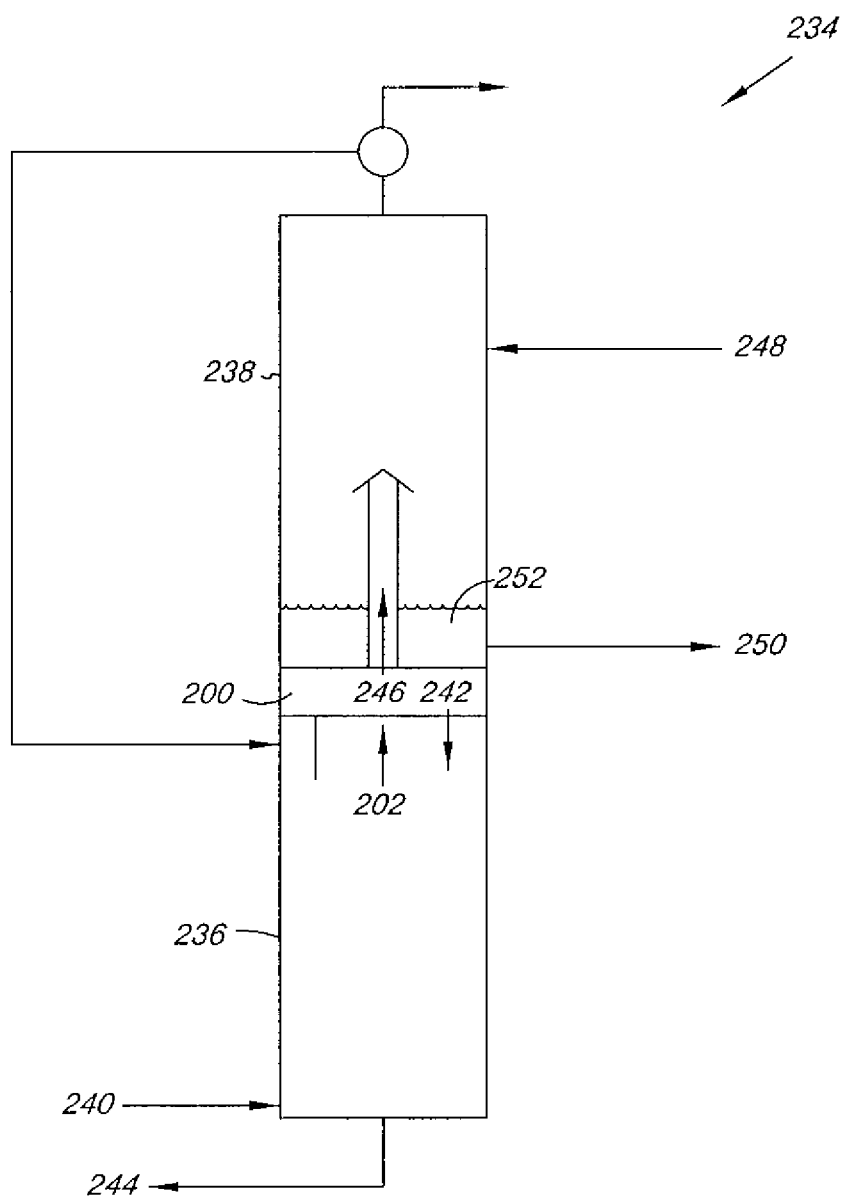
FIG. 2 provides an illustration of an ethylene oxide recovery column of the present disclosure.

FIG. 2 provides an illustration of an embodiment of an ethylene oxide recovery column according to the present disclosure. As shown in the embodiment of FIG. 2, the column 234 can include the condenser 200 positioned between a stripping portion 236 and a reabsorption portion 238. In some embodiments, the stripping portion 236 can be located in a lower half of the column 234 and the reabsorption portion 238 can be located in an upper half of the column 234.

The ethylene oxide recovery column 234, or column 234, as discussed herein, can have a diameter ranging front, for example, sixty-five (65) centimeters (cm) to six (6) meters (m) and have a height ranging from, for example, six (6) to sixty (60) m or more. As one skilled in the art will appreciate, in embodiments where the condenser 200 is located inside the column 234, the number of tubes in the tube bundle, as discussed herein, can be limited by the size of the column 234.

In some embodiments, the aqueous solution 240 entering the column 234 can include water, ethylene oxide, formaldehyde, and other light gases and impurities. Examples of further possible compounds in the aqueous solution 240 include methane, carbon dioxide, oxygen, nitrogen, argon, acetaldehyde, and ethylene, among others.

In some embodiments, the vapor stream 202 entering the condenser 200 can include between five (5) and about sixty (60) mole percent ethylene oxide. In addition, the condensed liquid 242 leaving the condenser 200 can include ethylene oxide in a range of about one (1) to about twenty (20) mole percent. The vapor stream 202 entering the condenser 200 can also include water in a range of about fifteen (15) to about eighty (80) mole percent, about five (5) to about two thousand (2,000) mole parts per million (ppm) formaldehyde, and about one (1) to about twenty (20) mole percent light gases and other impurities, as discussed herein.

As discussed herein, the condenser 200 is operated to remove approximately eighty (80) mole percent formaldehyde from the vapor stream 202 entering the condenser 200. As such, in some embodiments, the vapor inlet 202 can enter the condenser 200 at about 124,000 kilograms per hour (kg/hr) at about ninety-three (93) degrees Celsius (° C.) and at a pressure of about nineteen (19) pounds-force per square inch absolute (psia). The condenser 200, thus, can be operated to cool the vapor inlet to about thirty-seven (37)° C. with an approximate pressure drop along the tube side of the condenser 200 of about 0.2 (psi). To accomplish the appropriate temperature drop, the cooling water can be supplied to the condenser 200, as discussed herein, at about 33° C. with a flow of about three million ninety thousand (3,090,000) kg/hr.

The aqueous solution 240 produced from absorbing the dilute ethylene oxide mixture in the absorber, as discussed herein, can be introduced to the stripping portion 236 of the column 234. In the stripping portion 236, ethylene oxide can be removed from the aqueous solution 240 by converting a portion of the aqueous solution 240 to a gas phase. The gas phase, as used herein, is the portion of the aqueous solution 240 that undergoes a phase change and subsequently enters the condenser 200 of the present disclosure, as the vapor stream 202.

While a portion 202 of the aqueous solution 240 is converted to a gas phase, the remaining portion 244 of the aqueous solution 240 including water, ethylene oxide, and other compounds can be removed from the stripping portion 236 and routed back to the absorber, as discussed herein, to collect more ethylene oxide to be brought back to the column 234 in the aqueous solution 240.

As illustrated in FIG. 2, in some embodiments, the condenser 200 can be located at a top portion of the stripping portion 236 integral with the column 200. In such embodiments, the condensed liquid stream flowing down the internal surface of the tubes in the tube bundle can return directly to the stripping portion 236, and the ethylene oxide rich vapor stream 246 produced in the condenser 200 can be released at the top of the condenser 200. In some embodiments, the condensed liquid stream 242 flowing into the stripping portion 236 can include approximately eight (8) weight percent ethylene oxide.

In some embodiments, the ethylene oxide rich vapor stream 246 can be introduced to the reabsorption portion 238 of the column. In some embodiments, the reabsorption portion 238 can absorb ethylene oxide in the ethylene oxide rich vapor stream 246 by contacting with a water stream 248 to absorb the ethylene oxide content thereof.

As discussed herein, in some embodiments, the ethylene oxide stream 250 produced in the reabsorption portion 238 can be routed to the glycol unit reactor where ethylene oxide is converted to ethylene glycol by reaction with water. In some embodiments, water, in excess in the glycol unit reactor, can be distilled away from the ethylene glycol, condensed, and sent back to the column 234 in the form of the water stream 248 to reabsorb more ethylene oxide. The ethylene oxide stream 250 can also be routed for further purification, or for other reactions.

It is to be understood that the above description has been made in an illustrative fashion, and not a restrictive one. Although specific embodiments have been illustrated and described herein, those of ordinary skill in the art will appreciate that other component arrangements can be substituted for the specific embodiments shown. The claims are intended to cover such adaptations or variations of various embodiments of the disclosure, except to the extent limited by the prior art.

In the foregoing Detailed Description, various features are grouped together in exemplary embodiments for the purpose of streamlining the disclosure. This method of disclosure is not to be interpreted as reflecting an intention that any claim requires more features than are expressly recited in the claim. Rather, as the following claims reflect, inventive subject matter lies in less than all features of a single disclosed embodiment. Thus, the following claims are hereby incorporated into the Detailed Description, with each claim standing on its own as a separate embodiment of the invention.

Specific Embodiments of the Disclosure

The following examples are provided for illustrative purposes only and are not intended to limit the scope of the present disclosure. The examples provided herein disclose exemplary dimensions for the elements included in condensers of the present disclosure, where condensers including such elements thus sized can remove about eighty (80) Mole percent formaldehyde from an inlet stream including formaldehyde.

Example 1

| Element | Condenser 1 | Condenser 2 | Condenser 3 | Condenser 4 | Condenser 5 |
|---|---|---|---|---|---|
| Shell Internal Diameter (Inches) | 138 | 142 | 200 | 134 | 141.7 |
| Tube Outside Diameter (Inches) | 1.75 | 1.25 | 1.50 | 2.00 | 1.5 |
| Tube Internal Diameter (Inches) | 1.62 | 1.12 | 1.37 | 1.87 | 1.37 |
| Number of Tubes | 3,468 | 7,423 | 10,070 | 2,503 | 5,008 |
| Tube Length (Feet) | 32.50 | 21.00 | 26.25 | 39.00 | 26.2 |

What is claimed:

1. A method of operating a condenser, comprising:
    flowing a vapor stream including formaldehyde and water into a generally upright tube bundle in a vertical upflow reflux condenser, where a tube in the tube bundle has a length to outside diameter ratio of greater than about 170:1;
    flowing a cooling fluid on a shell-side of the vertical upflow reflux condenser to condense at least a portion of the vapor stream, where the condensed portion of the vapor stream and the vapor stream flow counter currently within the tube in the tube bundle and the condensed portion of the vapor stream forms a wetted tube internal surface area on each tube in the generally upright tube bundle;
    promoting methylene glycol formation by providing the wetted tube internal surface area for reacting formaldehyde and water to form methylene glycol; and
    maintaining the vapor stream velocity at a rate that provides a liquid residence time where formaldehyde condensed on the wetted internal surface area of each tube can react with water to form methylene glycol, removing at least sixty percent (60%) of formaldehyde from the vapor stream fed to the condenser.

2. The method of claim 1, where flowing the vapor stream into the generally upright tube bundle includes flowing the vapor stream at an exit velocity to form the wetted internal surface area on each tube in the generally upright tube bundle.

3. The method of claim 2, where the method includes collecting a portion of the condensed portion of the vapor stream exiting the tube bundle on a top tubesheet positioned at a top of the tube bundle, where condensed liquid flows down the internal surface area of each tube in the tube bundle.

4. The method of claim 3, including flowing the liquid reflux countercurrent to the vapor stream.

5. The method of claim 1, where the vapor stream velocity is about 8.5 feet per second (2.59 meters per second) or less.

6. The method of claim 1, where the vapor stream velocity is about ninety percent (90%) or less of a calculated critical flooding velocity at an inlet of the tube bundle.

7. The method of claim 1, where the method includes removing at least about eighty percent (80%) formaldehyde from the vapor stream fed to the condenser.

8. The method of claim 1, where the method includes removing at least about eighty-five percent (85%) formaldehyde from the vapor stream fed to the condenser.

9. The method of claim 1, where the liquid residence time is at least about 0.5 seconds.

* * * * *